United States Patent
Teich

(10) Patent No.: US 10,080,500 B2
(45) Date of Patent: Sep. 25, 2018

(54) SYSTEMS AND METHODS FOR MONITORING SUN EXPOSURE

(71) Applicant: FLIR Systems, Inc., Wilsonville, OR (US)

(72) Inventor: Andrew C. Teich, West Linn, OR (US)

(73) Assignee: FLIR Systems, Inc., Wilsonville, OR (US)

(*) Notice: Subject to any disclaimer, the term of this patent is extended or adjusted under 35 U.S.C. 154(b) by 157 days.

(21) Appl. No.: 14/880,090

(22) Filed: Oct. 9, 2015

(65) Prior Publication Data

US 2016/0100764 A1 Apr. 14, 2016

Related U.S. Application Data

(60) Provisional application No. 62/062,110, filed on Oct. 9, 2014.

(51) Int. Cl.
| | |
|---|---|
| *H04N 7/18* | (2006.01) |
| *A61B 5/01* | (2006.01) |
| *G06K 9/00* | (2006.01) |
| *A61B 5/00* | (2006.01) |

(52) U.S. Cl.
CPC .............. *A61B 5/015* (2013.01); *A61B 5/742* (2013.01); *G06K 9/00362* (2013.01); *H04N 7/188* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,107,123 A | * | 4/1992 | Shi | G01J 1/429 250/370.15 |
| 2004/0232359 A1 | * | 11/2004 | Fiset | A61N 5/0614 250/504 R |
| 2011/0025847 A1 | * | 2/2011 | Park | G06Q 10/06 348/143 |
| 2012/0056745 A1 | * | 3/2012 | Noguchi | G08B 21/24 340/573.1 |
| 2014/0288351 A1 | * | 9/2014 | Jones | A61N 5/06 600/9 |
| 2015/0206301 A1 | * | 7/2015 | Mestha | G06T 7/0012 382/128 |
| 2016/0006951 A1 | * | 1/2016 | Moghadam | G03B 35/02 348/164 |

* cited by examiner

*Primary Examiner* — Sathyanaraya V Perungavoor
*Assistant Examiner* — Janese Duley
(74) *Attorney, Agent, or Firm* — Haynes and Boone, LLP

(57) ABSTRACT

Systems and methods are provided for detecting overexposure of skin to ultraviolet light. A system may include a thermal imaging module that captures thermal images of a person's skin. Using the thermal images, the system may determine whether the person's skin has been or is being overexposed to ultraviolet light. The system may be a fixed camera system for monitoring an outdoor area, may be a mobile device having a thermal imaging module within or coupled to the mobile device, or may be part of a tanning system having an ultraviolet light source and a thermal imaging module. The overexposure may be detected in a thermal image based on a temperature of the person's skin, a change in the temperature of the person's skin over time or a temperature difference between portions of the person's skin.

18 Claims, 7 Drawing Sheets

SYSTEMS AND METHODS FOR MONITORING SUN EXPOSURE

CROSS-REFERENCE TO RELATED APPLICATIONS

This patent application claims the benefit of and priority to U.S. Provisional Patent Application No. 62/062,110 filed Oct. 9, 2014 and entitled "SYSTEMS AND METHODS FOR MONITORING SUN EXPOSURE" which is hereby incorporated by reference in its entirety.

TECHNICAL FIELD

One or more embodiments of the invention relate generally to infrared cameras and, more particularly, monitoring of sun exposure using infrared cameras.

BACKGROUND

Unfortunately, there currently exists no effective early warning or other detection system to detect or prevent overexposure to sunlight. As a result, there is a need for improved techniques for monitoring of exposure to ultraviolet light such as sunlight and for detection and prevention of sunburn.

SUMMARY

Systems and methods are disclosed, in accordance with one or more embodiments, which are directed to monitoring exposure to ultraviolet light such as sunlight. For example, sunburn monitoring, detection, and alert processes using infrared cameras may be provided.

When human skin is overexposed to ultraviolet light such as the ultraviolet light in sunlight, a "sunburn" can result in which skin cells are damaged by the overexposure. In particular, ultraviolet light such as UVa and UVb light included in the sunlight penetrates the layers of the skin and can directly damage the DNA within a skin cell and can also cause the release of free radicals in the various layers of the skin which can themselves further attack and damage skin cells. UVa light is typically understood to be light having wavelengths between about 315 nanometers (nm) and 400 nm and tends to pass through the epidermis layer of the skin and be absorbed in the underlying dermis potentially causing cell damage (e.g., DNA damage) and/or free radical release in the dermis. UVb light is typically understood to be light having wavelengths between about 280 nm and 315 nm and tends be absorbed in the epidermis potentially causing cell damage (e.g., DNA damage) and/or free radical release in the epidermis.

When skin cells are damaged in this way, an immune response is triggered which causes the erythema and nerve activation that are responsible for the typical redness and pain associated with a sunburn. The immune response can include increased blood flow to areas of the skin with damaged skin cells to provide white blood cells to remove the damaged cells and can result in inflammation and swelling.

Due to the increased blood flow, dilation of pores during the healing process of damaged skin cells, and/or other effects of overexposure to ultraviolet radiation such as direct heating of the skin by the sun, skin that has been or is being overexposed to ultraviolet light can radiate heat in excess of that radiated by healthy, undamaged skin that is not being overexposed. For example, depending on the ambient temperature, a person's skin can commonly have a temperature of around 90 degrees Fahrenheit (e.g., between 89 degrees and 92 degrees). Overexposed skin may have a relatively higher temperature such as a temperature around 96 degrees Fahrenheit. UV overexposed skin may therefore be detectable based on the temperature of the person's skin (e.g., a temperature over a sunburn threshold such as a 90 degree threshold, a 91 degree threshold, a 92 degree threshold, or other suitable sunburn threshold). Overexposed skin may also be detectable based on a temperature difference between various portions of the person's skin (e.g., a temperature difference that is more than a threshold such as more than 3 degrees, 5 degrees, six degrees, or other suitable difference threshold with respect to other portions of the person's skin). Temperature and/or temperature difference thresholds may be actively determined based on the ambient temperature in some embodiments. Various effects of UV overexposure on the skin may therefore be detectable in an infrared image of the skin such as a thermal image of the skin that includes absolute or relative temperature information.

The various effects of the ultraviolet light on the skin can affect the skin at various rates. For example, thermally detectable effects (e.g., almost instantaneous skin heating during direct exposure to sunlight and/or increased blood flow beginning as soon as cells begin to be damaged by the UV light) can occur before visibly or otherwise detectable effects (e.g., the visible redness (erythema) and pain of a sunburn that may not appear until several hours after the skin has been overexposed). Various effects of UV overexposure on the skin may therefore be detectable in an infrared image of the skin such as a thermal image of the skin before they are visibly or otherwise detectable.

According to various embodiments, systems and methods for infrared detection and/or monitoring of UV exposure are provided. In accordance with one embodiment, a system is provided that includes a thermal imaging module configured to capture a thermal image of a person's skin and a processor configured to determine, based on the thermal image, whether the person's skin is at risk of or has experienced overexposure to ultraviolet radiation.

For example, in one embodiment, a mobile device and/or a mobile device attachment having a thermal imager and a visible light imager may be used to capture a visible light image and a thermal image of a person or a portion thereof and to display an output image showing potentially sunburned areas such as an output image formed from the visible image of the person with areas of potential sunburn indicated by portions of the thermal image overlaid on the visible light image. For example, a parent, guardian, or other supervisor of a child playing outdoors may use a smart phone and an attached thermal/visible imager to perform a quick check of the child to determine whether additional sun protection is needed.

In accordance with another embodiment, a method is provided that includes capturing a thermal image of a person's skin and determining, based on the thermal image, whether the person's skin is at risk of or has experienced overexposure to ultraviolet radiation.

In accordance with another embodiment, a non-transitory machine readable medium is provided storing instructions that, when executed by a processor, cause the processor to perform a method, the method including receiving thermal image data; analyzing the thermal image data; and determining, based on the analyzing, areas of a person's skin having a risk of overexposure to ultraviolet light. The method may further include displaying an image based on the thermal image data that identifies the areas of the person's skin having the risk of overexposure to ultraviolet light. The method may further include providing, on a display, a warning of the risk of overexposure to ultraviolet light. The method may further include receiving non-thermal image data and providing a combined image based on the thermal image and the non-thermal image to a user.

The scope of the invention is defined by the claims, which are incorporated into this Summary by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the invention and their advantages are best understood by referring to the detailed description that follows. It should be appreciated that like reference numerals are used to identify like elements illustrated in one or more of the figures.

DETAILED DESCRIPTION

Systems and methods are disclosed herein to provide, according to various embodiments, monitoring of exposure to light such as ultraviolet light and detection of and alerts related to sunburn, particularly using thermal images. For example, an infrared camera may be used to capture thermal images of one or more persons or portions of a person's body. Thermal signatures of sunburn, impending sunburn or other overexposure or potential overexposure to light such as ultraviolet light may be extracted from the thermal images. In some embodiments, an alert may be generated to notify a user of the system or a system operator that a sunburn is occurring or has occurred.

Figure 1:
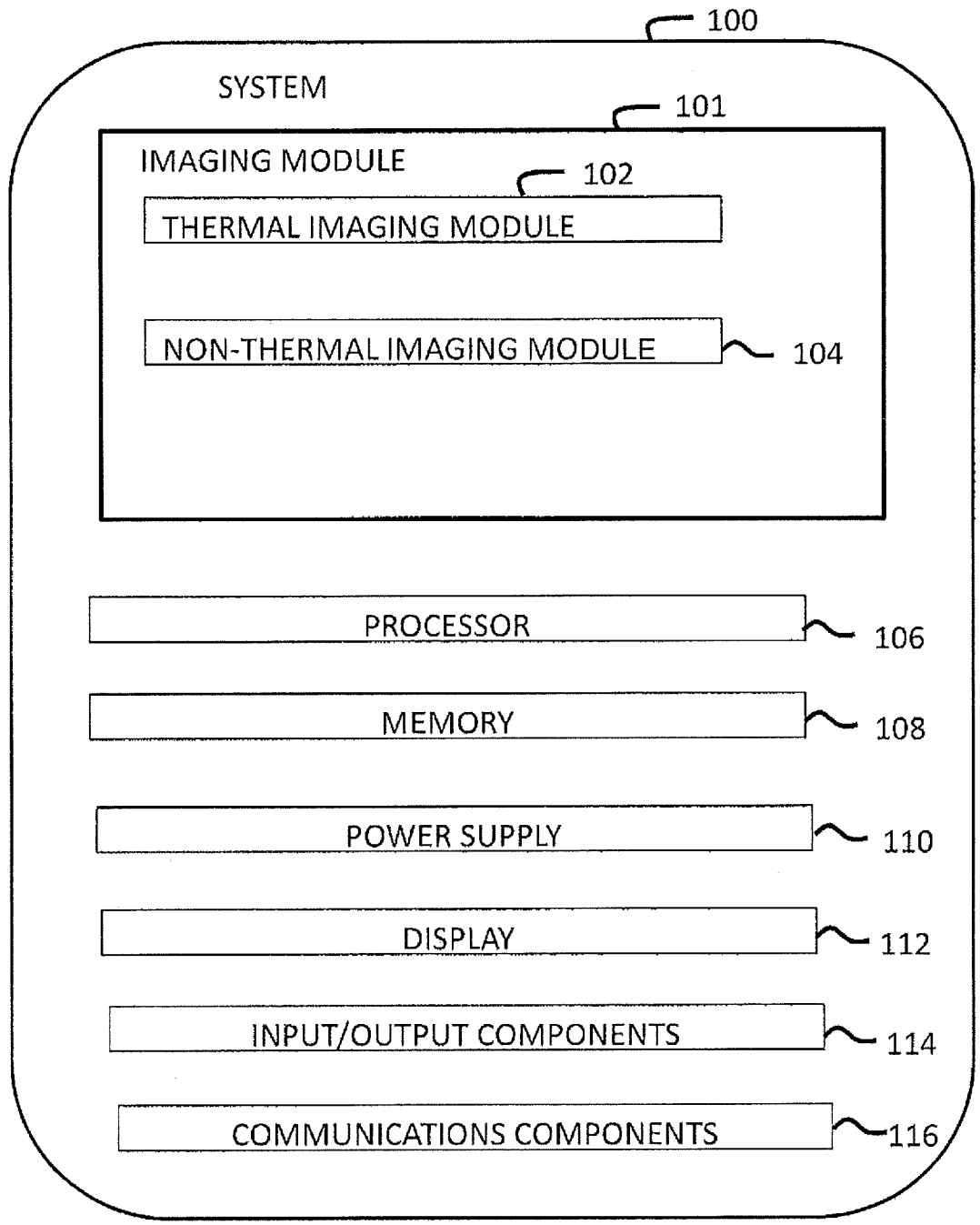
FIG. 1 shows a block diagram illustrating an imaging system for monitoring ultraviolet light exposure in accordance with one or more embodiments.

FIG. 1 illustrates a block diagram of a system (e.g., an imaging system such as an ultraviolet light exposure monitoring system having one or more imagine modules) for capturing and processing images and monitoring ultraviolet light exposure using the images in accordance with one or more embodiments. A system such as system 100 may include, in one implementation, an image capture component such as imaging module 101, a processing component such as processor 106, a memory component such as memory 108, a power supply 110 such as a battery, a display component such as display 112, input/output components 114, and/or communications components 116.

System 100 may represent, for example, an imaging system such as an infrared imaging system, a visible light imaging system, or a multi-band imaging system for capturing and processing images, such as still images and/or video images. In some embodiments, system 100 may represent any type of mobile device or larger system including an imaging module 101 and a processor that cooperate to monitor exposure, particularly of human skin (e.g., in sunlight or in a tanning facility) to ultraviolet light.

As examples, system 100 may include an infrared camera, a dual band imager that operates to sense reflected visible and/or short-wave infrared (SWIR) light for high resolution images and long-wave infrared (LWIR) radiation for thermal imaging, or an imager for sensing both short wave and long wave radiation simultaneously for providing independent image information. System 100 may comprise a portable device or a larger fixed system and may be incorporated, e.g., into a hand-held device, a vehicle, an outdoor installation, a tanning device or other system for monitoring exposure to ultraviolet light.

Imaging module 101 may include one or more imaging components for capturing images in response to light of various colors such as thermal imaging module 102 and/or non-thermal imaging module 104. Imaging module 101 may include various optical elements such as one or more lenses, mirrors, filters, or other optical elements for focusing or otherwise redirecting light of particular wavelengths onto image sensors of imaging modules 102 and/or 104. Thermal imaging module 102 may be used to capture thermal images such as long wave infrared (LWIR) and/or mid wave infrared wave (MWIR) images. Non-thermal imaging module 104 may be used to capture non-thermal images such as visible light images and/or short wave infrared (SWIR) images.

Thermal imaging module 102 may, in one embodiment, include one or more image detector elements such as infrared photodetector elements (e.g., any type of multi-pixel infrared detector, such as a focal plane array) for capturing thermal image data such as infrared image data (e.g., still image data and/or video data) representative of an scene. Thermal imaging module 102 may include an array of strained layer superlattice (SLS) detectors, uncooled detector elements (e.g., uncooled microbolometer sensors), cooled detector elements (e.g., detector elements such as photovoltaic or quantum structure elements that are cooled using a cryogen coupled to the array or using a refrigeration system), InSb detector elements, quantum structure detector elements, InGaAs detector elements, or other types of sensors.

Non-thermal imaging module 104 may, in one embodiment, include one or more image detector elements such as charge-coupled device (CCD) detector elements, complementary metal oxide semiconductor (CMOS) detector elements, or other types of sensors. In one implementation, imaging module 101 may be configured to generate digital image data representing incoming image light from a scene. Imaging module 102 may include one or more signal processing components such as analog-to-digital converters included as part of an image sensor or separate from the image sensor as part of system 100.

In various embodiments, processor 106 may include any type of a processor or a logic device (e.g., a programmable logic device (PLD) configured to perform processing functions). Processor 106 may be adapted to interface and communicate with components 102, 104, 108, 110, 112, 114, and/or 116 to perform method and processing steps and/or operations for system 100.

Memory 108 includes, in one embodiment, one or more memory devices adapted to store data and information, including for example image data such as infrared data and information. Memory 108 may include one or more various types of memory devices including volatile and non-volatile memory devices. Processing component 106 may be adapted to execute software stored in memory 108 so as to perform method and process steps and/or operations described herein.

Processor 106 may be implemented as any appropriate processing device (e.g., microcontroller, processor, application specific integrated circuit (ASIC), logic device, field programmable gate array (FPGA), circuit, or other device) that may be used to execute appropriate instructions, such as non-transitory machine readable instructions (e.g., software) stored on memory 108. For example, processor 106 may be configured to execute a sunburn detection application stored in memory 108.

Power supply 110 may include a portable power supply such as battery or solar cell power supply or may include a wired power supply. For example, in embodiments in which system 100 is implemented as mobile or portable device, power supply 110 may be a battery. In other embodiments, such as embodiments in which system 100 is implemented as a fixed system such as a system for monitoring an outdoor area such as an area around a swimming pool, a beach, a campground, a theme park, etc., power supply 110 may be a wired power supply that couples by a wire or cord to a power system (e.g., via a wall outlet).

Display 112 may include, in one embodiment, an image display device (e.g., a liquid crystal display (LCD) or various other types of generally known video displays or monitors). Processor 106 may be adapted to display image data and information such as thermal images, visible light images, combined or fused thermal and non-thermal images, alerts such as sunburn alerts or other information to a user on the display 112. Processor 106 may be adapted to retrieve image data and information from memory 108 and display retrieved image data and information on display 112. Display 112 may include display electronics, which may be utilized by processor 106 to display image data and/or other camera operations information (e.g., thermal images, combined thermal and visible light images, and/or alerts). Display 112 may be adapted to receive image data and information directly from imaging module 101 via the processor 106, or the image data and information may be transferred from memory 108 via processing component 106.

Input/output components 114 may include, in various embodiments, input components such as a keyboard, a microphone, buttons, or switches (as examples) and output components such as a speaker, a vibrator, a light source, or other audio, visual, or tactile output component. Input/output components may be used alone or in combination with display 112 to generate alerts for a user of system 100. For example, in one embodiment, thermal imaging module 102 may capture a thermal image of a portion of a human, processor 106 may detect a sunburn on the skin of the human based on the thermal image and a speaker may be used to generate an audible alert for the human or a system operator that a sunburn has been detected. In some embodiments, a visual alert may also be generated using display 112 or other visual output component (e.g., a flashing light).

Communications components 116 may include wireless and/or wired communications circuitry for sending and receiving signals to and from other portions of system 100 and/or other systems (e.g., via a cellular network, a wireless (WiFi) network, a wired network such as the internet or a local area network). For example, communications circuitry 116 may be used to transmit images captured using imaging module 101 to other components of system 100 or to remote computing equipment. Images captured by imaging module 101 may also be processed using processor 106 (e.g., to detect a sunburn or an impending sunburn) and processed data such as data indicating that a sunburn has been detected may be transmitted to other computing equipment using communications components 116. In various embodiments, components of system 100 may be combined and/or implemented or not, as desired or depending on the application or requirements, with system 100 representing various functional blocks of a related system.

Figure 2:
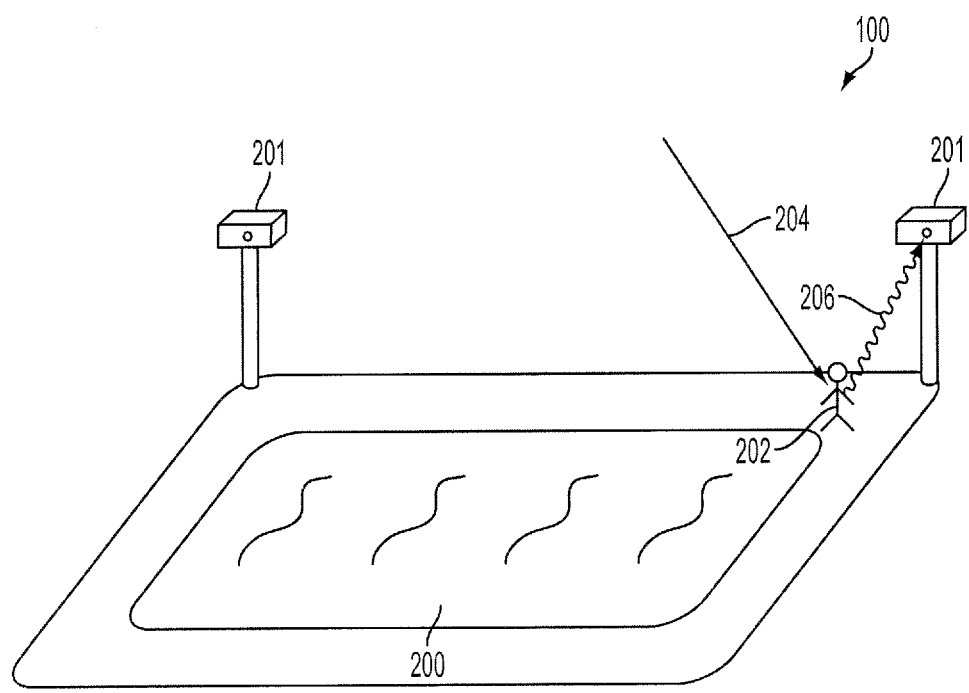
FIG. 2 shows a diagram illustrating an implementation example for an imaging system for monitoring sun exposure at an outdoor area in accordance with one or more embodiments.
Figure 3:
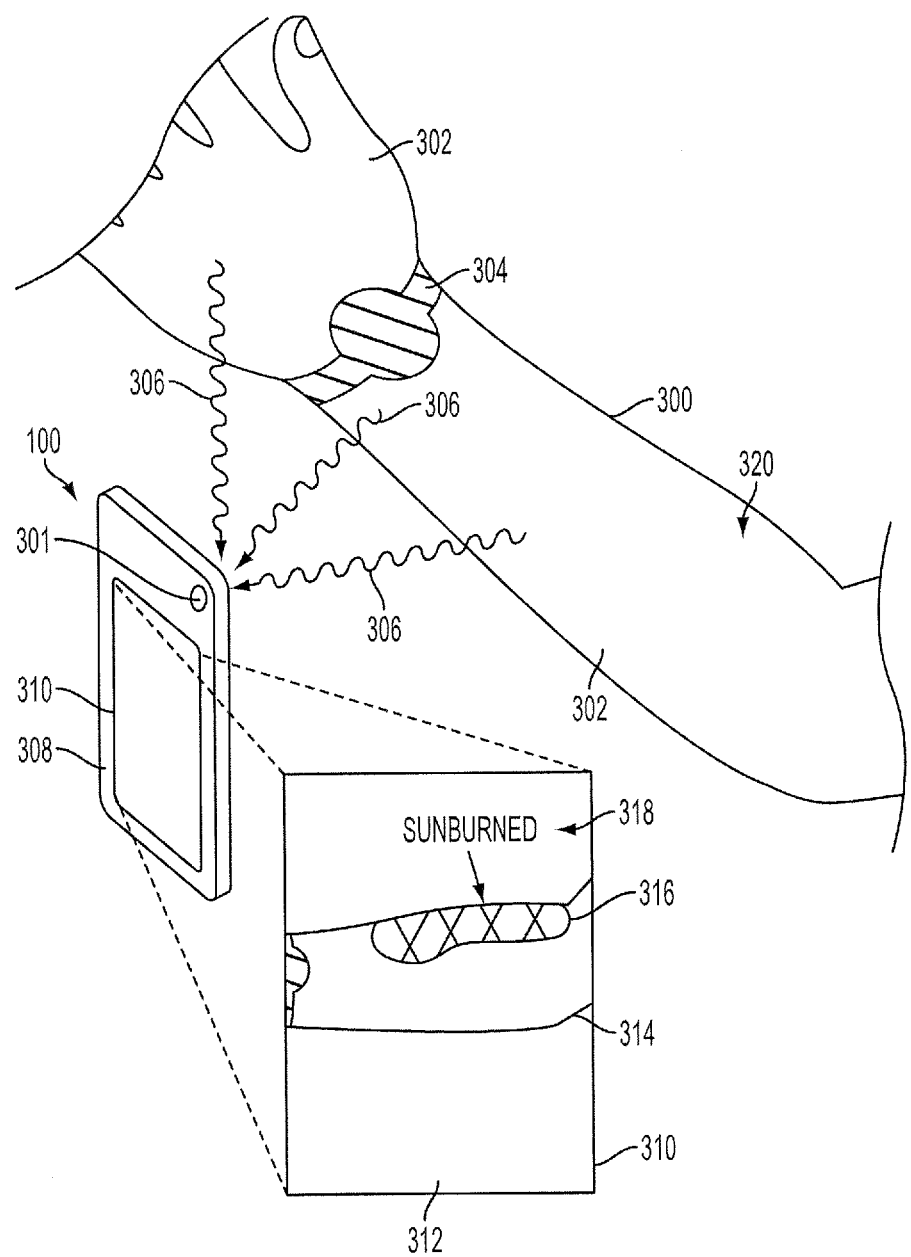
FIG. 3 shows a diagram illustrating an implementation example for an imaging system for monitoring ultraviolet light exposure using a mobile device in accordance with one or more embodiments.
Figure 4:
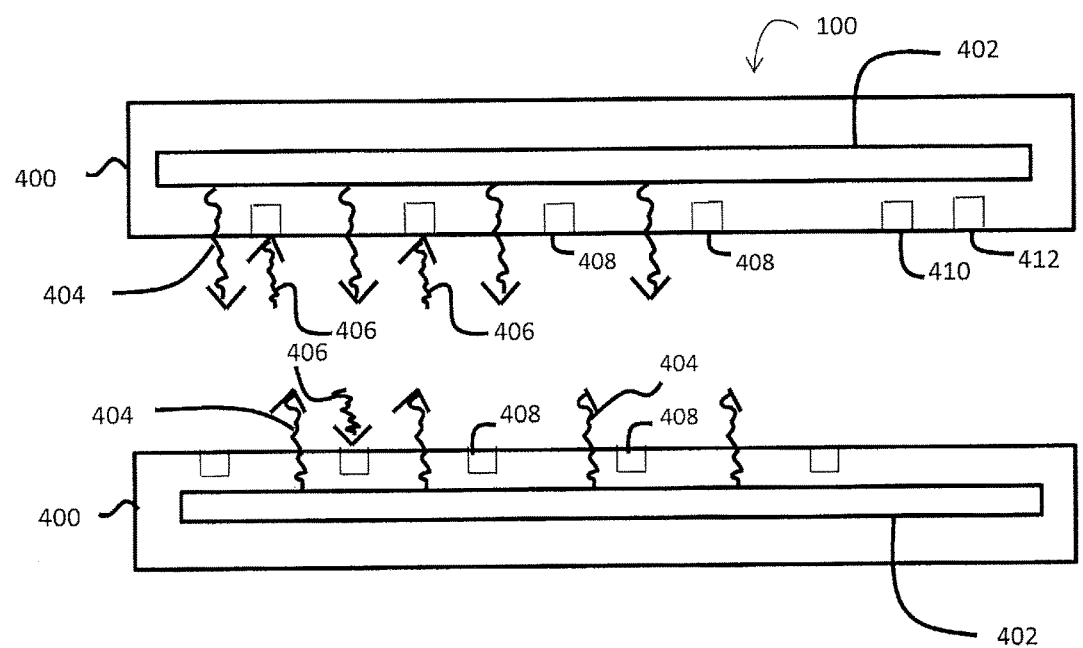
FIG. 4 shows a diagram illustrating an implementation example for an imaging system incorporated in a tanning system for monitoring ultraviolet light exposure in the tanning system in accordance with one or more embodiments.

FIGS. 2, 3, and 4 show various illustrative implementations of a system such as system 100 of FIG. 1 for monitoring of ultraviolet light exposure in accordance with various embodiments. In FIG. 2, system 100 is shown as a fixed camera system. In FIG. 3, system 100 is shown as a mobile device or a mobile device having a device attachment with a thermal and/or non-thermal imager having a sunburn detection application (e.g., an app such as a downloadable app or other application on the mobile device). In FIG. 4, system 100 is shown as a tanning system. Further details of each exemplary implementation in FIGS. 2, 3, and 4 are provided hereinafter.

In the example of FIG. 2, system 100 has been implemented as a fixed camera system for monitoring sun exposure at an outdoor area. In the particular example of FIG. 2, system 100 includes cameras 201 mounted at various locations around a swimming pool 200. Each camera 201 may include one or more imaging modules 101 (see FIG. 1) each having a field of view that includes some or all of the area in and/or around the swimming pool. Each camera 201 may include various other processing and/or communications components such as processor 106, memory 108, power supply 110, communications components 116 and/or other components of system 100 of FIG. 1.

Cameras 201 may periodically or continuously capture images of swimming pool 200 and the surrounding area of the swimming pool. For example, a thermal imaging module such as thermal imaging module 102 of FIG. 1 implemented in each camera 201 may be used to capture thermal images of swimming pool 200 and the surrounding area.

When a person such as person 202 spends time around a swimming pool, ultraviolet (UV) light such as UVa, UVb, or other UV light in sunlight 204 may be incident on the person's skin. Various people protect themselves from the UV light in sunlight using sunscreen or clothing, however, sunscreen can be washed away by water or sweat or worn away by clothing, people can forget to apply sunscreen, and people can become overexposed to ultraviolet light for any variety of similar reasons.

Cameras 201 may be used to capture images such as thermal images and/or non-thermal images of people such as person 202 using, for example, thermal emission 206 from the person's skin. System 100 may extract UV overexposure information from the captured images and may provide a warning to person 202 that a sunburn is possible, likely or has already occurred. The UV overexposure information may be extracted based on a temperature, color, and/or other feature of the person's skin in the captured images. In some embodiments, the thermal images may be radiometrically calibrated infrared images having calibrated temperature data corresponding to each pixel of the image.

According to an embodiment, a thermal image of person 202 may be used to determine that the temperature of the person's skin indicates the skin is being overexposed to UV light. In another embodiment, a change in the temperature of the person's skin may be used to determine that the skin is being overexposed to UV light (e.g., a change from the temperature of the person's skin determined from an earlier captured image). In another embodiment, a difference in the temperature of a portion of the person's skin with respect to another portion of the person's skin may be used to determine that the skin is being overexposed to UV light (e.g., a person's shoulders may exhibit a higher temperature than the person's arms if the skin on the person's shoulders is being or has been overexposed).

Thermal images may be used to detect the presence or risk of UV overexposure (e.g., sunburn) before skin redness appears (e.g., redness that can be detected visually or using non-thermal images). Thermal images can also be used detect the presence or risk of UV overexposure (e.g., sunburn) at night, in darkness or in other situations in which visible identification of skin damage is difficult or impossible (e.g., a user of a mobile device having a thermal imaging module and a sunburn detection application may capture thermal images of their skin before going to sleep at night to determine whether their skin is healthy enough to plan a trip to the beach the next day).

Non-thermal images may also be captured of person 202. Non-thermal images such as visible light images may be used, alone or in combination with the captured thermal images to detect and/or monitor UV overexposure and/or to track a particular person or portion of a person's skin. For example, a visible light image may be used alone or in combination with one or more thermal images to identify a particular person at the pool and to track that person so that changes in the person's skin temperature can be detected using the thermal images. In another example, a visible light image may be used alone or in combination with one or more thermal images to identify particular portions of a person such as to distinguish the person's shoulders, arms, legs, face, or other portions of the person so that differences in the person's skin temperature can be detected using the thermal images. In some embodiments, combined thermal and non-thermal images (e.g., a thermal image having high-contrast details from a non-thermal image superposed or overlaid on the thermal image) may be generated and presented to a user or a system operator and/or used to detect UV overexposure.

Although the example of FIG. 2 is described in the context of a swimming pool, it should be appreciated that cameras 201 may be provided for monitoring any suitable area such as a waterpark, a beach, a campground, a playground, a schoolyard, a park, a sporting event or concert seating area or other area in which people are exposed to sunlight.

When UV overexposure is detected for one or more people using cameras 201, an alert may be issued directly to the one or more people or to a system operator such as a lifeguard at the pool that the one or more people are at risk of or have already experienced UV overexposure. It may be determined that a person has already experienced UV overexposure (e.g., is sunburned) if thermal emission from the person's skin is consistent with thermal emission from sunburned skin (e.g., has a temperature, an intensity, a temperature difference or a temperature change in excess of a sunburn threshold). It may be determined that a person is at risk of UV overexposure if thermal emission from the person's skin has a temperature, an intensity, a temperature difference or a temperature change over time in excess of that emitted by healthy skin but below a threshold for sunburned skin.

In the example of FIG. 3, system 100 has been implemented as mobile device 308 (e.g., a mobile phone, tablet or camera device) having a camera 301. In other embodiments, camera 301 may be a camera of a mobile device attachment (not shown) for mobile device 308 (e.g., a device attachment having a thermal imaging module, a non-thermal imaging module, a processor, a memory and/or a battery that communicatively and mechanically attaches to device 308 to provide thermal imaging capabilities to device 308). Camera 301 may include one or more imaging modules 101 (see FIG. 1). Device 308 and/or a thermal imaging attachment for device 308 may include various other processing and/or communications components such as processor 106, memory 108, power supply 110, communications components 116 and/or other components of system 100 of FIG. 1.

Camera 301 may be operated to capture an image of a person or a portion of a person such as a person's arm 300. Device 308 may include, for example, a sunburn detection and/or monitoring application (e.g., stored in the form of non-transitory instructions in memory 108 that, when executed by processor 106 cause the camera to capture one or more images and cause the processor to detect potential or existing sunburn based on the one or more images). For example, a thermal imaging module such as thermal imaging module 102 of FIG. 1 and/or a non-thermal imaging module implemented in camera 301 may be used to capture one or more thermal images and/or non-thermal images of arm 300 and/or any other portions of the person for which the person desires to determine whether UV overexposure has occurred or is occurring.

As shown in FIG. 3, the person's skin may include an exposed portion 302 that shows effects of UV exposure and another portion 304 that does not show UV exposure effects. In the example of FIG. 3, portion 304 may have been covered by a watch while the person's arm was exposed to sunlight or other UV light. Due to the UV exposure, portion 302 of the persons arm skin may emit thermal radiation 306 of a different temperature or in a different amount from portion 304. Thermal images of portions 302 and 304 may indicate the differences in the thermal radiation from portions 302 and 304 and may indicate that some or all of portion 302 is being or has been overexposed to UV light. Differences in temperature between portions 302 and 304 and/or various parts of portion 302 may be detected in a thermal image or in a series of thermal images (e.g., if the user scans device 308 across an area of skin while capturing thermal images and/or storing temperatures determined from various thermal images). Characteristic patterns (e.g., spatial patterns and/or temperature gradient patterns) may also be detected (e.g., at the border between portions 302 and 304 or between various parts of portion 302) that are characteristic of UV overexposure.

Device 308 may include a display 310 (e.g., an implementation of display 112 of FIG. 1). Display 310 may be used to provide the user of device 308 with an image 312 and/or an alert to the user if potential or existing UV overexposure is detected based on the thermal images.

In the example of FIG. 3, image 312 includes an image 314 of a portion of arm 300 and indicators 316 and 318. Indicator 316 may, for example, be a portion of a thermal image in which potential or existing UV overexposure is detected that has been overlaid on a visible light image of the arm 300. However, this is merely illustrative. In other embodiments, indicator 316 may be a boundary of a sunburned region that is overlaid on a thermal, non-thermal or combined thermal and non-thermal image or a colorized portion of a thermal image (e.g., a color portion of a greyscale thermal image or a color thermal image having a particular color such as a blue color or a red color in the sunburned region). Indicator 316 may be a static indicator or may be a blinking, flashing, or other dynamic indicator. In general, image 312 may be an output image generated based on any suitable combination of thermal and/or non-thermal images.

In one embodiment, a thermal image, a non-thermal image or a combined or fused thermal and non-thermal image may be provided with indicators for burning portions of a person's skin, portions that are at-risk or nearly burning, and/or portions that are healthy or not burning (e.g., portions that are adequately protected by clothing or sunscreen). For example, indicator 316 may include a red portion indicating those areas of a person's skin that are burning, a yellow portion indicating those areas that are getting close to being burned, and a green portion for those that are adequately protected. Indicator 316 may be generated based on thermal images of the person's skin an added to a visible light image of the person's skin in the appropriate locations, according to an embodiment. Indicator 316 may be an opaque indicator that blocks portions of image 312 or may be a partially transparent indicator that allows viewing of image 312 through the indicator.

In some embodiments, an additional indicator such as indicator 318 may be provided by display 310. In the example of FIG. 3, indicator 318 includes text (e.g., "SUNBURNED") and an arrow pointing to indicator 316 or a portion of indicator 316. However, this is merely illustrative. In various embodiments, indicator 318 may be provided without indicator 316, indicator 316 may be provided without indicator 318 and/or indicator 318 may include any suitable visual indicator of a sunburn in image 312 such as an arrow, a circle or other indicators as desired. As shown in FIG. 3, the portion 320 of arm 300 that is indicated by indicator 316 may not have any apparent signs (e.g., to an unaided human eye) of UV overexposure and may therefore only be detectable using the thermal imaging capabilities of system 100.

In the example of FIG. 4, system 100 has been implemented as a tanning system having thermal imaging UV overexposure monitoring capabilities. Tanning systems such as tanning beds typically emit UV light onto a person in the system in order to provide skin tanning effects for the user. Some tanning systems limit the amount of time a person can spend in the tanning system in order to attempt to prevent UV overexposure. However, due to differences in the response of various people's skin to UV light, it can be difficult to predict the appropriate limit to prevent overexposure and possible skin damage. A system such as the system of FIG. 4 may therefore be provided that includes thermal and/or non-thermal imaging capabilities for monitoring UV exposure based on images of the skin itself.

In the implementation of FIG. 4, system 100 includes tanning bed structures 400 each including a light source 402 such as a UV light source that provides light 404 such as UV light onto a user (not shown) in the tanning bed. Due to the exposure to UV light 404, the temperature, color, and/or other features of the user's skin may change and light such as thermal emissions 406 may be emitted from the user's skin toward one or more cameras 408. Cameras 408 may be disposed in the tanning bed structures 400, attached to the tanning bed structures 400 or mounted separately from the tanning bed structure and positioned to view the user. Cameras 408 may be formed as an integral portion of the tanning bed structures or a UV overexposure system having camera 408 may be provided as a standalone system that can be added to or arranged with tanning bed structures or other tanning system structures to monitor UV exposure before, during, and/or after tanning operations.

Each camera 408 may include one or more imaging modules 101 (see FIG. 1) each having a field of view that includes some or all of the area in and/or around the tanning bed. Each camera 408 may include various other processing and/or communications components such as processor 106, memory 108, power supply 110, communications components 116 and/or other components of system 100 of FIG. 1 and/or processing and/or communications components may be provided elsewhere in tanning bed portions 400 or remote from the tanning bed and in communication with cameras 408.

Cameras 408 may periodically or continuously capture images of a user of the tanning bed before, during, and/or after exposure to UV light 404 to monitor the user for UV overexposure. For example, a thermal imaging module such as thermal imaging module 102 of FIG. 1 implemented in each camera 408 may be used to capture thermal images of the user for monitoring of UV exposure of the user.

In the example implementation of FIG. 4, system 100 includes an alert component 410 and a shutoff component 412. Alert component 410 may be used to provide an audible, visual or other alert when UV overexposure or risk of UV overexposure of a user is detected using, for example, thermal images of the user. Shutoff component 412 may be arranged to automatically turn off light sources 402 when UV overexposure or risk of UV overexposure of a user is detected using, for example, thermal images of the user.

Providing only thermal imaging modules in cameras 408 may also provide the additional advantage of protecting the user's privacy by avoiding capturing visible light images of the user.

Figure 5:
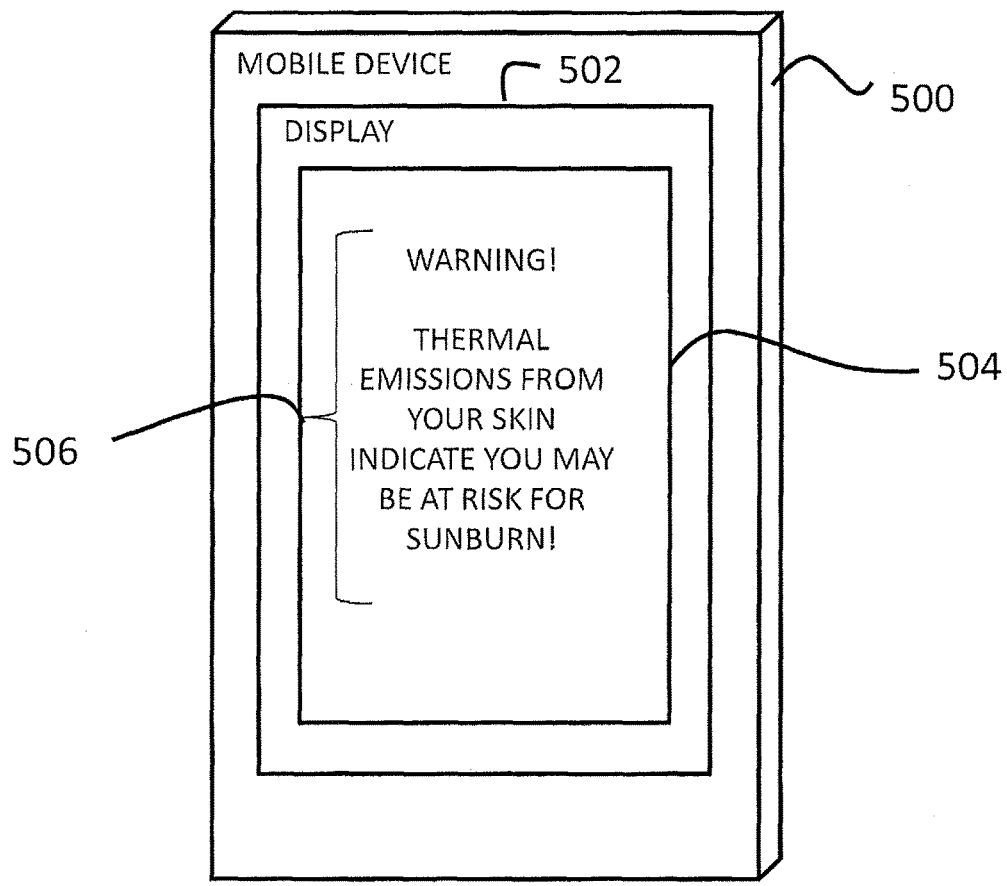
FIG. 5 shows a block diagram illustrating a sunburn alert that may be provided to a user on a mobile device in accordance with one or more embodiments.

FIG. 5 shows an exemplary mobile device and shows how a display of the mobile device may be used to provide a UV overexposure alert to a user of the mobile device. As shown in FIG. 5, a mobile device such as mobile device 500 may include display 502. Display 502 may be used to provide an alert 504 to a user of the mobile device. Alert 504 may inform the user that they are at risk of or have experienced overexposure to UV radiation (e.g., that the user has a sunburn or is at risk of a sunburn). Alert 504 may include text 506 as shown (e.g., "WARNING! THERMAL EMISSIONS FROM YOUR SKIN INDICATE YOU MAY BE AT RISK FOR SUNBURN!"). However, the text of alert 504 is merely illustrative. In general, any suitable text, images, icons, or other visual, audible, or tactile alert may be provided using mobile device 500 to inform the user that they are at risk of or already have a sunburn.

The mobile device may include a processor and an imaging module and may generate alert 504 responsive to detecting a sunburn or skin in the process of being overexposed to UV light (e.g., sunlight). However, this is merely illustrative. In some embodiments mobile device 500 may receive the alert from another device or a portion of system 100 such as a fixed monitoring camera that has detected, using thermal images of the user, that the user has or is getting a sunburn.

In one embodiment, a thermal image or a combined or fused thermal and non-thermal image (not shown) may be displayed to the user within alert 504 along with information indicating where in the image the sunburn has been detected. The information indicating where the sunburn has been detected may include an overlaid boundary of a burned region, a detected temperature or color of the burned region, a temperature difference between a burned region and a healthy region, an arrow, a circle or other indicators as desired.

In some embodiments, an alert may be provided to a system operator instead of or in addition to a user. For example, in the implementation example of FIG. 2, a lifeguard may be provided with a device that receives alerts for pool attendees based on images captured using cameras 201 (see FIG. 2).

Figure 6:
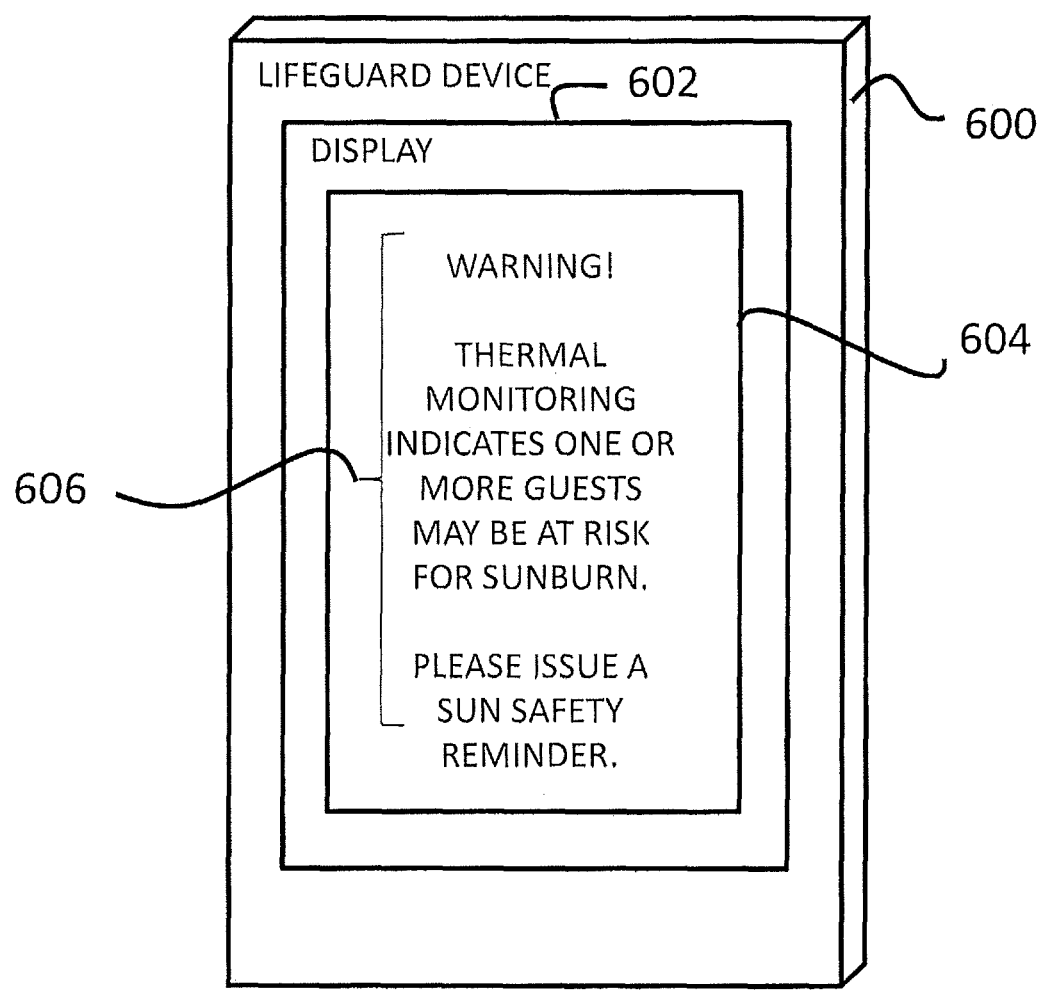
FIG. 6 shows a block diagram illustrating a sunburn alert that may be provided to a lifeguard on a lifeguard device in accordance with one or more embodiments.

FIG. 6 shows an exemplary lifeguard device and shows how a display of the lifeguard device may be used to provide a UV overexposure alert to a system operator such as a lifeguard. As shown in FIG. 6, a lifeguard device such as lifeguard device 600 may include a display such as display 602. Display 602 may be used to provide a system operator such as a lifeguard with an alert 604 informing the lifeguard that one or more people at the body of water the lifeguard is monitoring may be at risk for sunburn. As shown, alert 604 may include text 606 informing the lifeguard of a sunburn or a sunburn risk (e.g., "WARNING! THERMAL MONITORING INDICATES THAT ONE OR MORE GUESTS MAY BE AT RISK FOR SUNBURN. PLEASE ISSUE A SUN SAFETY REMINDER."). However, the text of alert 604 is merely illustrative. In general, any suitable text, images, icons, or other visual, audible, or tactile alert may be provided using lifeguard device 600 to inform the lifeguard that one or more guests at an outdoor area such as a swimming pool, beach or other outdoor area as described herein is at risk of or already has a sunburn. The alert may, for example, include instructions for the lifeguard to issue a sun safety reminder to a crowd in general or to an individual or individuals.

Figure 7:
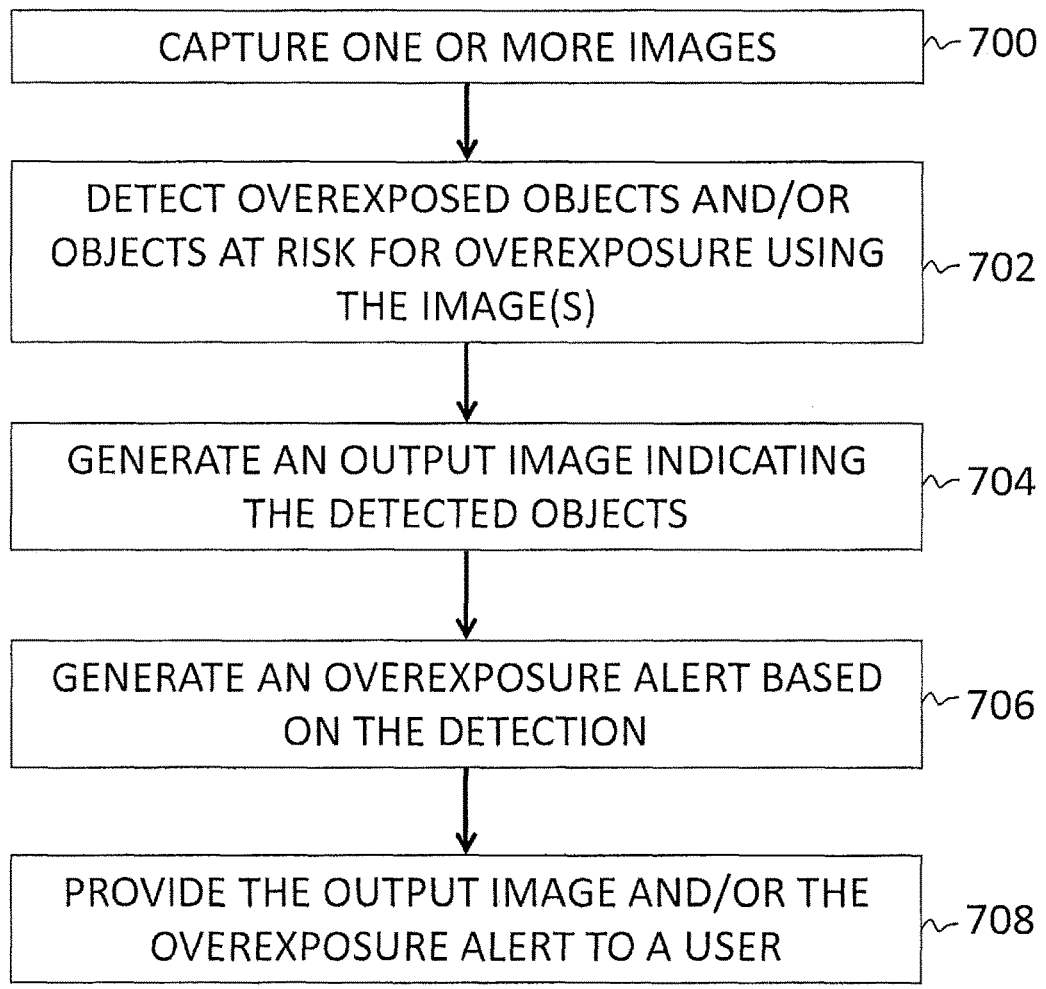
FIG. 7 shows a flow diagram illustrating operations that may be performed for monitoring ultraviolet light exposure in accordance with one or more embodiments.

Illustrative operations that may be used for image based UV overexposure monitoring are shown in FIG. 7 in accordance with one or more embodiments.

At block 700, one or more images such as thermal images and/or non-thermal images may be captured. The captured image(s) may include an image of an area in which one or more people are located or may be an image of a portion of a person's body. Capturing the image(s) may include capturing one or more images using a fixed camera installation having one or more thermal and/or non-thermal imaging modules such as the fixed installations described above in connection with FIGS. 2 and 4 or a mobile camera such as the camera of the mobile device of FIG. 3. Capturing the image(s) may include capturing one or more images responsive to a user input such as a user clicking a real or virtual shutter button or may include periodically or continuously capturing images.

At block 702, one or more overexposed (e.g., UV overexposed or sunburned) objects (e.g., people or portions of a person) and/or one or more objects at risk for overexposure may be detected using the image. For example, as described herein the one or more images may include a thermal image that indicates that a person or a portion of a person's skin is emitting thermal radiation at a temperature or an intensity that indicates that the person's skin or a portion thereof is being or has been overexposed to UV light such as sunlight.

At block 704, an output image indicating the detected objects may be generated. The output image may be a user viewable thermal image, a visible light image having a thermal image overlay on the detected overexposed or at-risk object, a fused thermal and non-thermal image having high contrast features of a visible light image overlaid on the thermal image, an enhanced thermal image colorized or otherwise adapted to indicated the detected objects, a thermal, non-thermal, or combined thermal and non-thermal image having one or more indicators overlaid on or otherwise displayed with the image to indicate the detected objects, or any other suitable image in which the detected objects are identified or identifiable for a human user.

At block 706, an overexposure alert may be generated based on the detection of the one or more overexposed objects and/or objects at risk of overexposure. As described herein, an overexposure alert may include text, an image, a sound, a light, a vibration or other suitable alert information provided via a user device or fixed system component.

At block 708, the output image and/or the overexposure alert may be provided to a user such as a user of a mobile device having a sunburn detection application (e.g., when the user scans or captures images of themselves or a child while the sunburn detection application (app) is in operation on the mobile device).

Where applicable, various embodiments of the invention may be implemented using hardware, software, or various combinations of hardware and software. Where applicable, various hardware components and/or software components set forth herein may be combined into composite components comprising software, hardware, and/or both without departing from the scope and functionality of the invention. Where applicable, various hardware components and/or software components set forth herein may be separated into subcomponents having software, hardware, and/or both without departing from the scope and functionality of the invention. Where applicable, it is contemplated that software components may be implemented as hardware components and vice-versa.

Software, in accordance with the invention, such as program code and/or data, may be stored on one or more computer readable mediums. It is also contemplated that software identified herein may be implemented using one or more general purpose or specific purpose computers and/or computer systems, networked and/or otherwise. Where applicable, ordering of various steps described herein may be changed, combined into composite steps, and/or separated into sub-steps to provide features described herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected is:

1. A system, comprising:
 a thermal imaging module configured to capture a thermal image of a person's skin; and a processor configured to detect, based on the thermal image, whether the person's skin is at risk of or has experienced overexposure to ultraviolet radiation based on a detected temperature of the person's skin from the thermal image, a detected change in temperature of the person's skin over time as determined from the thermal image and at least one additional thermal image, and/or a detected temperature difference between a first portion of the person's skin and a second portion of the person's skin from the thermal image, wherein the processor is further configured to generate an overexposure alert if it is determined that the person's skin is at risk of or has experienced overexposure to ultraviolet radiation.

2. The system of claim 1, further comprising a display, wherein the processor is further configured to generate the overexposure alert on the display if it is determined that the person's skin is at risk of or has experienced overexposure to ultraviolet radiation, wherein the processor is configured to generate the overexposure alert on the display for the detected skin temperature exceeding approximately ninety two degrees Fahrenheit and/or the detected temperature difference between the first portion of the person's skin and the second portion of the person's skin greater than a five degrees Fahrenheit threshold.

3. The system of claim 2, further comprising a non-thermal imaging module configured to capture a non-thermal image of the person's skin, wherein the processor is further configured to:
generate a combined image based on the thermal image and the non-thermal image; and
provide the combined image on the display.

4. The system of claim 3, wherein the combined image comprises the non-thermal image and an indicator based on the thermal image, wherein the indicator indicates a location in the non-thermal image of at least a portion of the person's skin that is sunburned.

5. The system of claim 1, further comprising a plurality of cameras configured to view an outdoor area to be monitored, wherein the thermal imaging module is disposed in a selected one of the plurality of cameras.

6. The system of claim 1, wherein the thermal imaging module and the processor are a thermal imaging module and a processor of a mobile device or a mobile device attachment, and wherein the processor is further configured to generate the overexposure alert as a vibration, a light, and/or a sound on the mobile device or mobile device attachment.

7. The system of claim 1, further comprising at least one tanning bed structure having an ultraviolet light source, wherein the thermal imaging module is disposed in the tanning bed structure.

8. The system of claim 7, further comprising an alert component configured to generate an overexposure alert if it is determined that the person's skin is at risk of or has experienced overexposure to ultraviolet radiation.

9. The system of claim 8, further comprising a shutoff switch configured to turn off the ultraviolet light source if it is determined that the person's skin is at risk of or has experienced overexposure to ultraviolet radiation.

10. A method, comprising:
capturing a thermal image of a person's skin;
displaying the thermal image; and
processing the thermal images to determine whether the person's skin is at risk of or has experienced overexposure to ultraviolet radiation by:
detecting a temperature of the person's skin from the thermal image;
detecting a change in temperature of the person's skin over time from the thermal image and at least one additional thermal image; and/or
detecting a temperature difference between a first portion of the person's skin and a second portion of the person's skin from the thermal image; and
generating an overexposure alert if it is determined that the person's skin is at risk of or has experienced overexposure to ultraviolet radiation.

11. The method of claim 10, further comprising generating the overexposure alert on a display if it is determined that the person's skin is at risk of or has experienced overexposure to ultraviolet radiation, wherein the generating comprises generating the overexposure alert on the display for the detected skin temperature exceeding approximately ninety two degrees Fahrenheit and/or the detected temperature difference between the first portion of the person's skin and the second portion of the person's skin greater than a five degrees Fahrenheit threshold.

12. The method of claim 10, wherein the capturing comprises capturing the thermal image using a thermal imaging module of a mobile device or a mobile device attachment, and wherein the generating an overexposure alert comprises generating a vibration, a light, and/or a sound on the mobile device or mobile device attachment.

13. The method of claim 10, further comprising generating ultraviolet light using an ultraviolet light source in at least one tanning bed structure and wherein the capturing comprises capturing the thermal image using a thermal imaging module disposed in the tanning bed structure.

14. The method of claim 13, further comprising turning off the ultraviolet light source if it is determined that the person's skin is at risk of or has experienced overexposure to the ultraviolet light.

15. A non-transitory machine readable medium storing instructions that, when executed by a processor, cause the processor to perform a method, the method comprising:
receiving thermal image data of a person's skin;
processing the thermal image data, wherein the processing comprises:
detecting a temperature of the person's skin from the thermal image;
detecting a change in temperature of the person's skin over time from the thermal image and at least one additional thermal image; and/or
detecting a temperature difference between a first portion of the person's skin and a second portion of the person's skin from the thermal image; and
determining, based on the processing, areas of a person's skin having a risk of overexposure to ultraviolet light; and
generating an overexposure alert if it is determined that the person's skin is at risk of or has experienced overexposure to ultraviolet radiation.

16. The non-transitory machine readable medium of claim 15, wherein the method further comprises displaying an image based on the thermal image data that identifies the areas of the person's skin having the risk of overexposure to ultraviolet light.

17. The non-transitory machine readable medium of claim 15, wherein the method further comprises providing, on a display of a mobile device or a mobile device attachment, a warning of the risk of overexposure to ultraviolet light, and wherein the generating an overexposure alert comprises generating a vibration, a light, and/or a sound on the mobile device or the mobile device attachment.

18. The non-transitory machine readable medium of claim 15, wherein the method further comprises:
  receiving non-thermal image data; and
  providing a combined image based on the thermal image data and the non-thermal image data to a user.

* * * * *